(12) United States Patent
Goto

(10) Patent No.: US 8,582,842 B2
(45) Date of Patent: Nov. 12, 2013

(54) IMAGE DISPLAY DEVICE, METHOD AND PROGRAM

(75) Inventor: Yoshihiro Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 372 days.

(21) Appl. No.: 13/054,997

(22) PCT Filed: Jul. 22, 2009

(86) PCT No.: PCT/JP2009/063076
§ 371 (c)(1),
(2), (4) Date: Jan. 20, 2011

(87) PCT Pub. No.: WO2010/010880
PCT Pub. Date: Jan. 28, 2010

(65) Prior Publication Data
US 2011/0123077 A1    May 26, 2011

(30) Foreign Application Priority Data
Jul. 25, 2008  (JP) ................................ 2008-192648

(51) Int. Cl.
  *G06K 9/00* (2006.01)
  *G06K 9/48* (2006.01)
(52) U.S. Cl.
  USPC .......................................... 382/128; 382/199
(58) Field of Classification Search
  USPC .................... 382/128–132; 345/667; 600/425
  See application file for complete search history.

(56) References Cited

U.S. PATENT DOCUMENTS 6,252,599 B1 *   6/2001   Natsuko et al. ............... 345/419
2007/0183644 A1 *   8/2007   Matsumoto ................... 382/131

FOREIGN PATENT DOCUMENTS

| JP | 09-237352 | * | 9/1997 |
| JP | 11-56832 | | 3/1999 |
| JP | 2000-51207 | | 2/2000 |
| JP | 2008-100107 | | 5/2008 |
| JP | 2008-167802 | | 7/2008 |

OTHER PUBLICATIONS

International Search Report in PCT/JP2009/063076.

* cited by examiner

*Primary Examiner* — Amara Abdi
(74) *Attorney, Agent, or Firm* — Cooper & Dunham LLP

(57) ABSTRACT

A pair of static magnetic field generating means disposed so as to sandwich a space in which an examination target is disposed, magnetic field generating means that applies high-frequency magnetic field and gradient magnetic field to an examination target disposed in the static magnetic field, and reception means that receives a nuclear magnetic resonance signal generated by the examination target are provided. The reception means has a predetermined coil pattern, and contains a reception coil which can be formed in a cylindrical shape. The reception coil has a flexible portion and a rigid portion which are alternately arranged along the peripheral direction when it is designed in a cylindrical shape, and the flexible portion has a flexible board on which a part of the predetermined coil pattern is mounted, and a bubble-containing organic resin portion covering both the surfaces of the flexible board.

14 Claims, 19 Drawing Sheets

F I G . 2
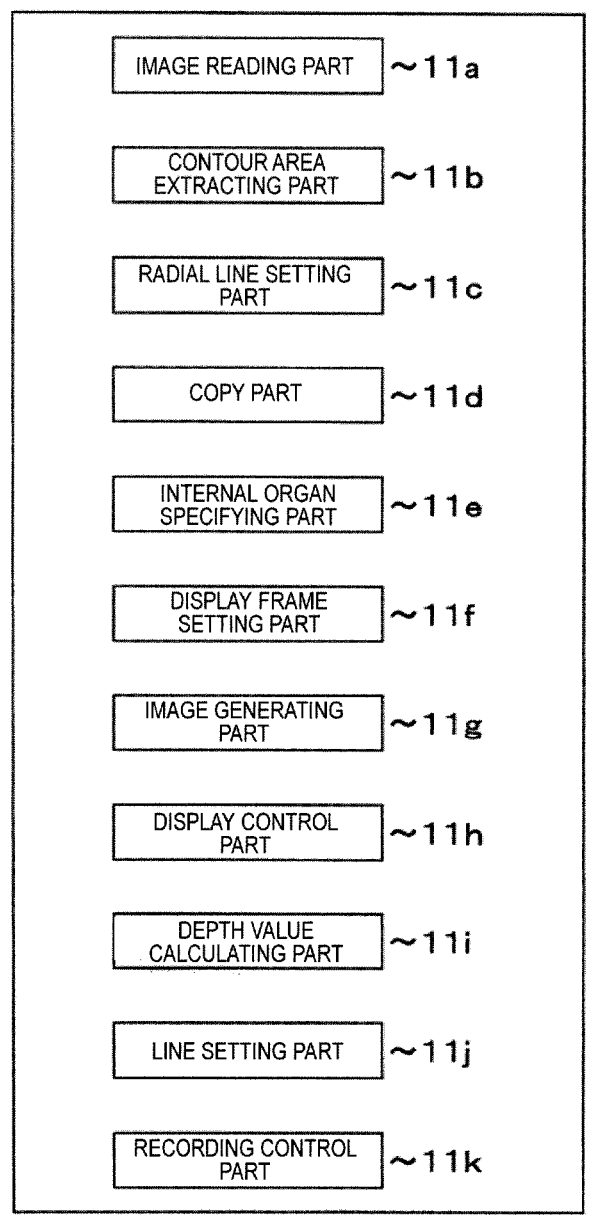

F I G . 4 B
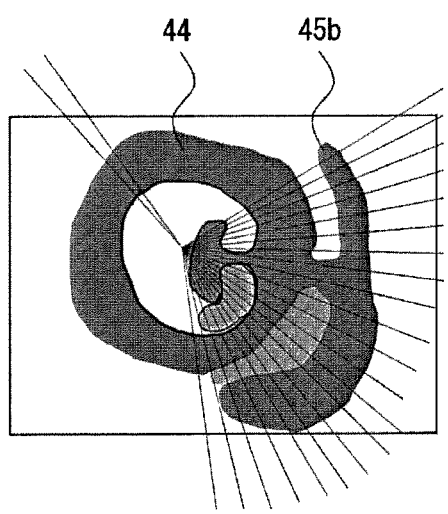

F I G . 6
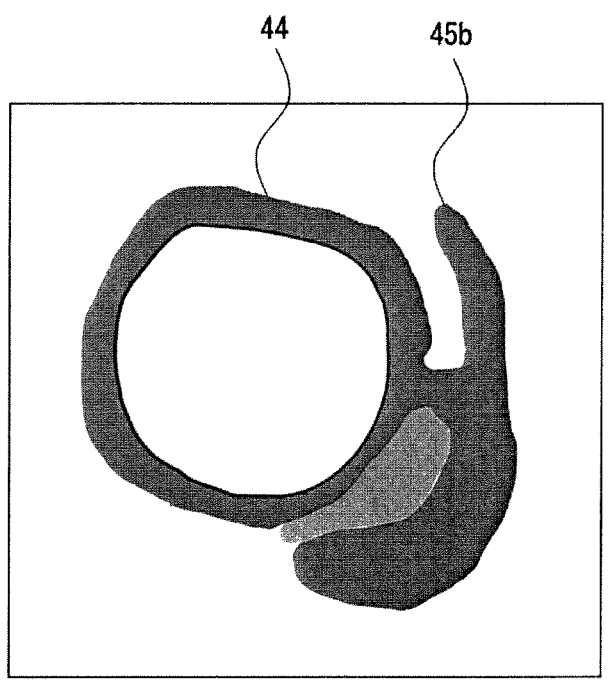

FIG. 7
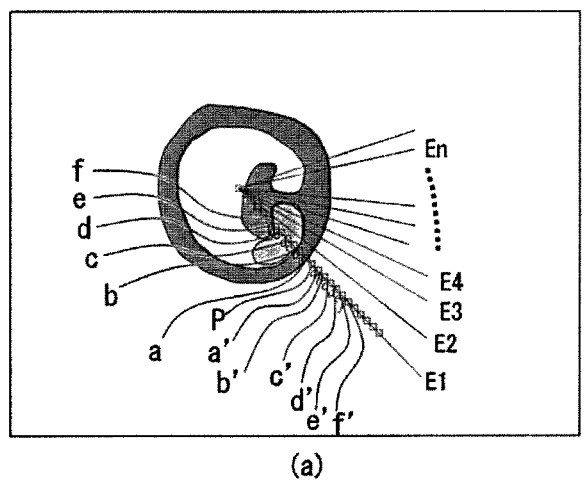
(a)
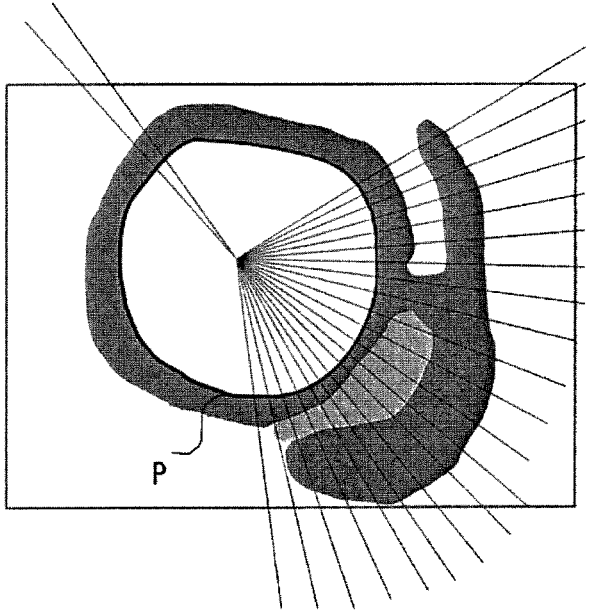
(b)

FIG. 8
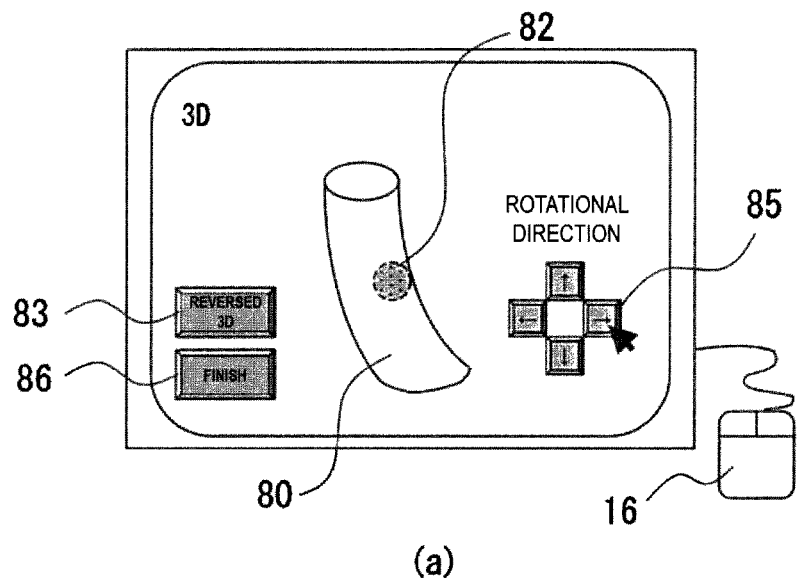
(a)
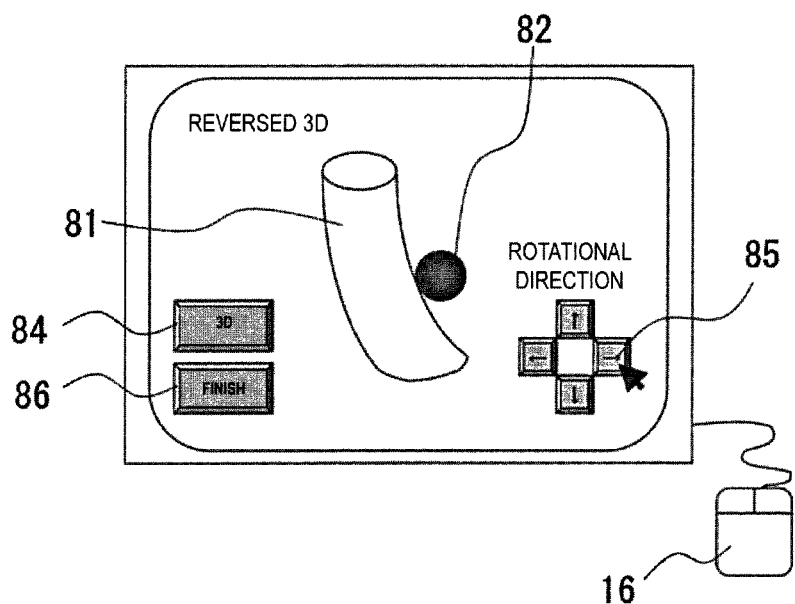
(b)

FIG. 11
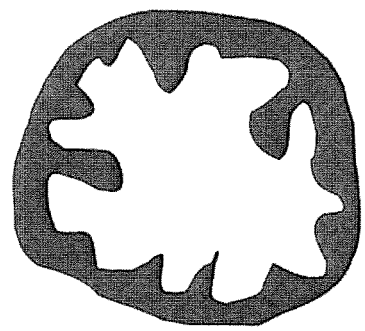
(a)
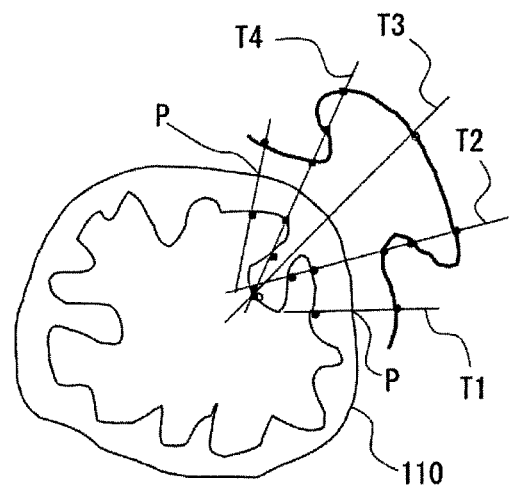
(b)

F I G . 1 2
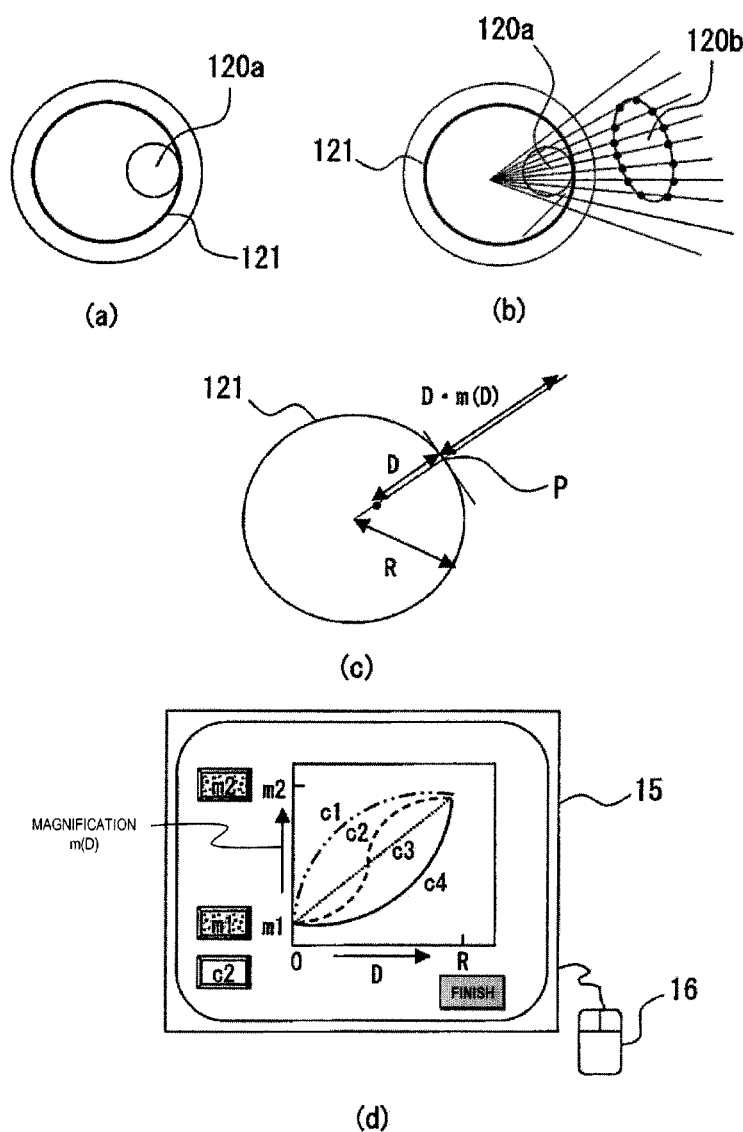

FIG. 13
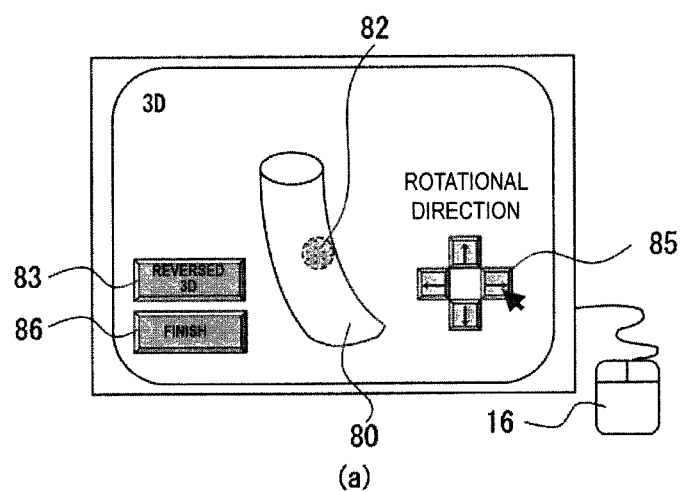
(a)
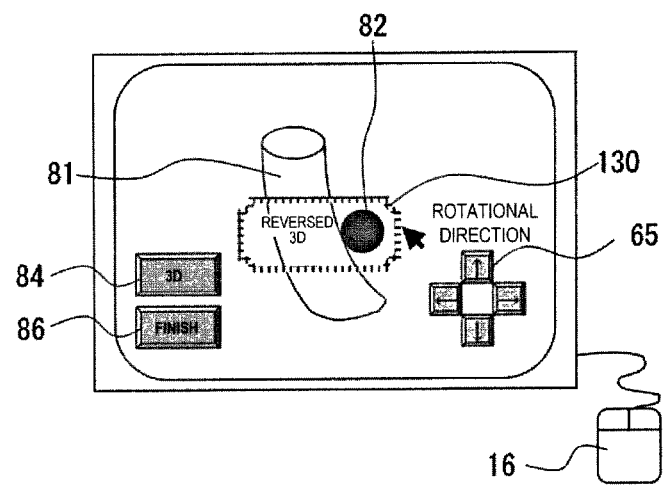
(b)

F I G . 1 6
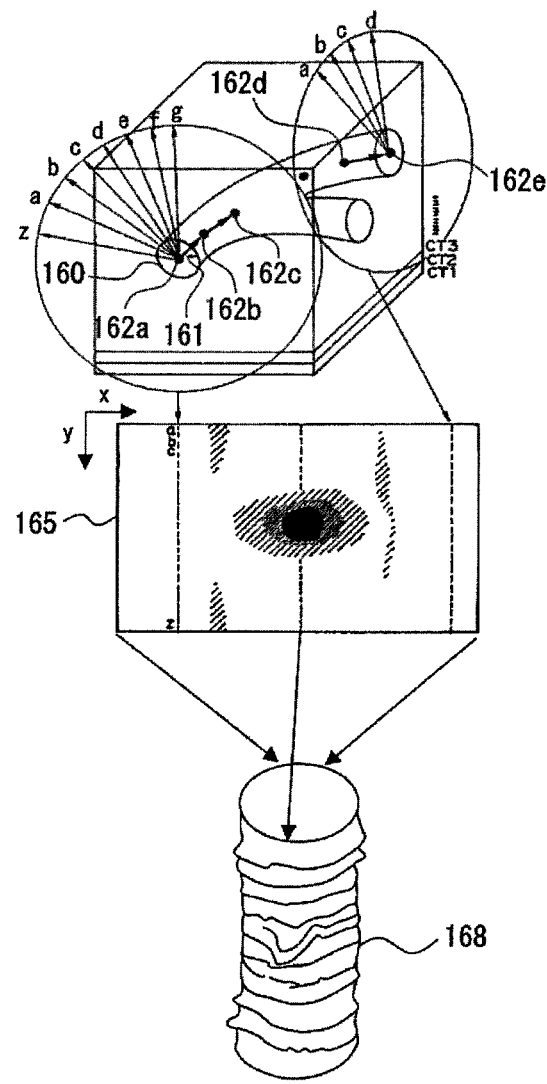

IMAGE DISPLAY DEVICE, METHOD AND PROGRAM

TECHNICAL FIELD

The present invention relates to image display device, method and program, and particularly to a technique of enhancing visibility of an inner surface of a hollow organ.

BACKGROUND ART

Patent Document 1 discloses a three-dimensional image constructing method for perspectively coordinate-transforming an examinee having an internal space to a coordinate system on any point-of-view plane to obtain a two-dimensional image in a volume image obtained by stacking many tomographic images, and shading the two-dimensional image while the distance between a virtual line light source provided in the examinee and a contour point of the inside of the examinee and the distance between the outside of the examinee and the point-of-view plane are reflected to the two-dimensional image, thereby obtaining a three-dimensional image in which shading corresponding to the inner surface shape and the outer surface shape of the examinee is applied to the outer surface of the examinee.

Prior Art Document

Patent Document

Patent Document 1: JP-A-9-237352

SUMMARY OF THE INVENTION

Problem to be Solved by the Invention

However, according to the three-dimensional image constructing method described above, even when the shading of the inside of the examinee is applied to the outer surface of the examinee, the shading of the outer surface itself of the examinee is not varied in a concavo-convex shape. Therefore, there is a problem that it is insufficient to check the unevenness of the inside of the examinee.

The invention has been implemented in view of the foregoing problem, and has an object to provide image display device, method and program that can easily check the unevenness of a hollow organ of an examinee.

Means of Solving the Problem

In order to attain the above object, image display device, method and program according to the invention are characterized by generating and displaying a reversed image in which the shape of an inner surface of a hollow organ is displayed as a concavo-convex shape of an outer surface of the hollow organ in an original image as a medical image.

More specifically, an image display device according to the invention is characterized by comprising: contour area extracting means that extracts a contour area comprising plural contour points at which a body tissue of an examinee is imaged, from a medical image obtained by imaging a hollow organ having a cavity space inside the body tissue of the examinee; radial line setting means that sets a radial center in a cavity area of the medical image in which the cavity space is imaged, sets a radial line extending from the radial center to the contour area and sets a boundary point at one point on the radial line; copy means that copies, onto the radial line at the outside of the boundary point, image information at a pixel point that is located on the radial line and at the inside of the boundary point; image generating means that generates, on the basis of the copied image information of the pixel point, a reversed image in which an area at the inside of the boundary point is depicted at the outside of the boundary point; and image display means that displays the reversed image.

In this specification, "copy" means both of the processing of leaving data of an original source and further attaching image information to a copy destination, and the processing of deleting image information of a copy source and attaching image information to a copy destination, that is, so-called cut & paste processing.

Furthermore, in this specification, "reversed image" means both of a two-dimensional reversed image and a pseudo three-dimensional reversed image unless it is particularly limited.

Still furthermore, in this specification, "reversed image is displayed" contains all of a case where only a two-dimensional reversed image is displayed, a case where only a pseudo three-dimensional reversed image is displayed and a case where both of two-dimensional and pseudo three-dimensional reversed images are selectively or simultaneously displayed.

An image display device according to the invention is characterized by comprising: contour area extracting means that extracts a contour area comprising plural contour points at which a body tissue of an examinee is imaged, from a medical image obtained by imaging a hollow organ having a cavity space inside the body tissue of the examinee; line setting means that sets a line being perpendicular to a tangent line of a curved line based on a shape of the contour area and passing through a contact point on a curved line based on a shape of the contour area; copy means that copies, onto the line at the outside of the contact point, image information at a pixel point which is located on the line and at the inside of the contact point; image generating means that generates, on the basis of the copied image information of the pixel point, a reversed image in which an area at the inside of the contact point is depicted at the outside of the contact point; and image display means that displays the reversed image.

Furthermore, an image display device according to the invention is characterized by comprising: contour area extracting means that extracts a contour area comprising plural contour points at which a body tissue of an examinee is imaged, from a medical image obtained by imaging a hollow organ having a cavity space inside the body tissue of the examinee; line setting means that sets a line being perpendicular to a tangent line of a curved line based on a shape of the contour area and passing through a contact point on a curved line based on a shape of the contour area; copy means that copies image information at a pixel point located on the line and at the inside of the contact point onto the line at the outside of the contact point; image generating means that generates, on the basis of the copied image information of the pixel point, a two-dimensional reversed image in which an area at the inside of the contact point is depicted at the outside of the contact point; recording control means that controls to record the two-dimensional reversed image into a data storage device; and display means that generates and displays a pseudo three-dimensional reversed image on the basis of the two-dimensional reversed image recorded in the data storage device.

An image display device according to the invention is characterized by comprising: contour area extracting means that extracts a contour area comprising plural contour points at which a body tissue of an examinee is imaged, from a medical image obtained by imaging a hollow organ having a cavity space inside the body tissue of the examinee; line setting means that sets a line which is perpendicular to a tangent line of an innermost side contour curved line comprising an innermost side contour point array of the contour area and passes through an innermost side contour point serving as a contact point on the innermost side contour curved line; copy means that copies image information of a pixel point located on the line and at the outside of the innermost side contour point onto the line at the inside of the innermost side contour point; image generating means that generates, on the basis of the copied image information of the pixel point, a reversed image in which an area at the outside of the innermost side contour point is depicted at the inside of the innermost side contour curved line; and image display means that displays the reversed image.

Furthermore, a image display device according to the invention is characterized by comprising: contour area extracting means that extracts an innermost side contour point out of a contour area comprising a plurality of contour points at which a body tissue of an examinee is imaged in a medical image comprising a volume image obtained by stacking, in a body axis direction of the examinee, a plurality of tomographic images which are obtained by imaging a hollow organ having a cavity space inside the body tissue of the examinee; depth calculating means that sets, in the medical image, a virtual line light source in a cavity area in which the cavity space is imaged, calculates the distance from the virtual line light source to the innermost side contour point at each position of the virtual line light source while moving the position of the virtual line light source along a running direction of the hollow organ, and calculates depth value information for associating the position of the virtual line light source in the running direction of the hollow organ with the distance from the position concerned to the innermost side contour point; image generating means that coordinate-transforms the depth value to the distance in the running direction of the hollow organ on the basis of the depth value information, and shades the outer surface of a coordinate-transformed image in accordance with the distance at each position in the running direction of the hollow organ, thereby generating a reversed image in which the shading of an inner surface of the hollow organ is depicted on an outer surface of the hollow organ; and image display means that displays the reversed image.

An image display method according to the invention is characterized by comprising: a step of extracting a contour area comprising a plurality of contour points at which a body tissue of an examinee is imaged, from a medical image obtained by imaging a hollow organ having a cavity space inside the body tissue of the examinee; a step of setting a radial center in a cavity area of the medical image in which the cavity space is imaged, sets a radial line extending from the radial center to the contour area and sets a boundary point at one point on the radial line; a step of copying, onto the radial line at the outside of the boundary point, image information at a pixel point which is located on the radial line and at the inside of the boundary point; a step of generating, on the basis of the copied image information of the pixel point, a reversed image in which an area at the inside of the boundary point is depicted at the outside of the boundary point; and a step of displaying the reversed image.

Furthermore, an image display method according to the invention is characterized by comprising: a step of extracting a contour area comprising a plurality of contour points at which a body tissue of an examinee is imaged, from a medical image obtained by imaging a hollow organ having a cavity space inside the body tissue of the examinee; a step of copying image information of a pixel point located on the line and at the inside of the contact point onto the line at the outside of the contact point; a step of generating, on the basis of the copied image information of the pixel point, a reversed image in which an area at the inside of the contact point is depicted at the outside of the contact point; and a step of displaying the reversed image.

Still furthermore, an image display method according to the invention is characterized by comprising: a step of extracting a contour area comprising plural contour points at which a body tissue of an examinee is imaged, from a medical image obtained by imaging a hollow organ having a cavity space inside the body tissue of the examinee; a step of setting a line being perpendicular to a tangent line of a curved line based on a shape of the contour area and passing through a contact point on a curved line based on a shape of the contour area; a step of copying image information at a pixel point located on the line and at the inside of the contact point onto the line at the outside of the contact point; a step of generating, on the basis of the copied image information of the pixel point, a two-dimensional reversed image in which an area at the inside of the contact point is depicted at the outside of the contact point; a step of recording the two-dimensional reversed image into a data storage device; and a step of generating and displaying a pseudo three-dimensional reversed image on the basis of the two-dimensional reversed image recorded in the data storage device.

Still furthermore, an image display method according to the invention is characterized by comprising: a step of extracting a contour area comprising plural contour points at which a body tissue of an examinee is imaged, from a medical image obtained by imaging a hollow organ having a cavity space inside the body tissue of the examinee; a step of setting a line which is perpendicular to a tangent line of an innermost side contour curved line comprising an innermost side contour point array of the contour area and passes through an innermost side contour point serving as a contact point on the innermost side contour curved line; a step of copying image information of a pixel point on the line and located at the outside of the innermost side contour point onto the line at the inside of the innermost side contour point; a step of generating, on the basis of the copied image information of the pixel point, a reversed image in which an area at the outside of the innermost side contour point is depicted at the inside of the innermost side contour curved line; and a step of displaying the reversed image.

An image display method according to the invention is characterized by comprising: a step of extracting an innermost side contour point out of a contour area comprising a plurality of contour points at which a body tissue of an examinee is imaged in a medical image comprising a volume image obtained by stacking, in a body axis direction of the examinee, a plurality of tomographic images which are obtained by imaging a hollow organ having a cavity space inside the body tissue of the examinee; a step of setting, in the medical image, a virtual line light source in a cavity area in which the cavity space is imaged, calculating the distance from the virtual line light source to the innermost side contour point at each position of the virtual line light source while moving the position of the virtual line light source along a running direction of the hollow organ, and calculating depth value information for associating the position of the virtual line light source in the running direction of the hollow organ with the distance from the position concerned to the innermost side contour point; a step of coordinate-transforming the depth value to the distance in the running direction of the hollow organ on the basis of the depth value information, and shading the outer surface of a coordinate-transformed image in accordance with the distance at each position in the running direction of the hollow organ, thereby generating a reversed image in which the shading of an inner surface of the hollow organ is depicted on an outer surface of the hollow organ; and a step of displaying the reversed image.

An image display program according to the invention is characterized by making a computer execute any one of the foregoing image display methods.

Effect of the Invention

According to the invention, the inside and outside of the hollow organ can be displayed while interchanged with each other, and thus there can be provided image display device, method and program which can easily check unevenness of a hollow organ of an examinee.

BRIEF DESCRIPTION OF THE DRAWINGS

FIG. 1 is a diagram showing the construction of an image display system using an image display device according to the invention.

[FIG. 2] FIG. 2 is a block diagram showing an image processing program installed in an image display device 10.

FIG. 3 is a flowchart showing the flow of the processing according to a first embodiment.

FIG. 4A is a schematic diagram showing a state that a radial center and a radial line are set in a hollow organ extracted from a medical image.

[FIG. 4B] FIG. 4B is a schematic diagram showing the processing of copying a contour point.

FIG. 4C is a schematic diagram showing an example in which a curved line circumscribing an innermost side contour curved line is used as a boundary curved line.

FIG. 4D is a schematic diagram showing an example in which a curved line connecting points of any ratio in a contour area is used as a boundary curved line.

FIG. 5 is a schematic diagram showing a state that a radial center is set at a position deviated from the center of gravity of the cross-section of a hollow organ.

[FIG. 6] FIG. 6 is a schematic diagram showing a reversed image obtained after the processing of FIG. 4B.

[FIG. 7] FIG. 7 is a schematic diagram showing an example in which enlargement/reduction processing is executed at the copying time.

[FIG. 8] FIG. 8 is a schematic diagram showing a screen display example.

FIG. 9 is a schematic diagram showing a CT image as an original image and a reversed 3D generated on the basis of the CT image.

FIG. 10 is a flowchart showing the flow of the processing according to a second embodiment.

[FIG. 11] FIG. 11 is a schematic diagram showing the processing of the second embodiment.

[FIG. 12] FIG. 12 is a schematic diagram showing the content of the processing according to a third embodiment.

[FIG. 13] FIG. 13 is a schematic diagram showing a screen display example displayed according to a fourth embodiment.

FIG. 14 is a schematic diagram showing an example in which a circle larger than an outermost side contour curved line is used as a boundary curved line.

FIG. 15 is a schematic diagram showing a processing example according to a sixth embodiment.

[FIG. 16] FIG. 16 is a schematic diagram showing the content of the processing according to a seventh embodiment.

EMBODIMENTS FOR CARRYING OUT THE INVENTION

Figure 1:
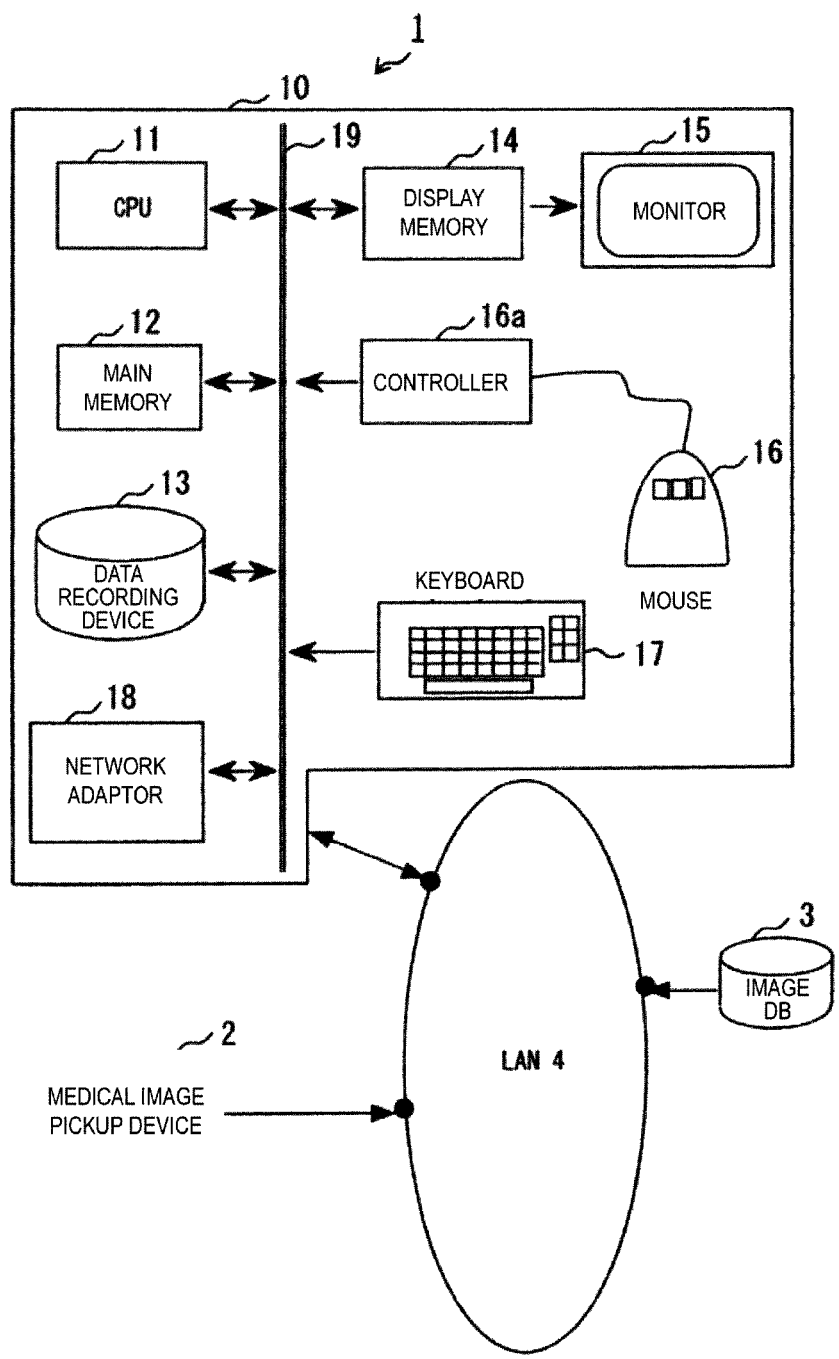
[FIG. 1]

Embodiments according to the invention will be described with reference to the accompanying drawings. In all the figures to describe the embodiments of the invention, the elements having the same functions are represented by the same reference numerals, and the repetitive description thereof is omitted.

FIG. 1 is a diagram showing the construction of an image display system using an image display device according to the invention. The image display system 1 is constructed by connecting, through LAN 4, a medical image pickup device 2 such as an X-ray CT device, a magnetic resonance imaging device (hereinafter referred to as "MRI device"), an ultrasonic device (hereinafter referred to as "US device") or the like disposed in a hospital or a health clinic center, an image data base (image DB) 3 for storing medical images and an image display device 10 to which the invention is applied. An image is stored into the medical image pickup device 2 or the image DB 3 through LAN 4.

The image display device 10 mainly comprises a central processing unit (CPU) 11 for controlling the operation of the respective constituent elements, a main memory 12, a data recording device 13, a display memory 14 for temporarily storing display data, a monitor 15 comprising a liquid crystal monitor, CRT or the like, a pointing device (not shown) such as a mouse 16, a trackball, or a touch panel for operating soft switches on the monitor 15, a controller 16a for the pointing device described above, a keyboard 17 having keys and switches for setting various kinds of parameters, a network adaptor 18 for connecting the image display device 10 to a network such as LAN 4, a telephone line, or the Internet, and a data bus 19 for connecting the respective constituent elements. The data recording device 13 may be a storage device such as a memory or a hard disk which is internally or externally provided to the image display device 10, a device for writing/reading data into/from a detachable external medium, or a device for transmitting/receiving data to/from an external storage device through the network.

FIG. 2 is a block diagram showing an image processing program installed in the image display device 10.

The image processing program has an image reading part 11a for reading a medical image, a contour area extracting part 11b for extracting, from the medical image, a contour area constructed by plural contour points at which a hollow organ comprising a body tissue surrounding a cavity space is imaged, a radial line setting part 11c for setting a radial line and a boundary point P in the contour area, a copy part 11d for copying image information of a contour point at the inside of the boundary point P to the outside of the boundary point, an internal organ specifying part 11e for specifying an imaged desired internal organ in the medical image, a display frame setting part 11f for setting, on a pseudo three-dimensional image of the hollow organ, a display frame for displaying a reversed image corresponding to a site of the pseudo three-dimensional image, an image generating part 11g for generating a reversed image in which the shape of an inner surface (inner wall curved line) of the hollow organ is depicted at the outside of the hollow organ, a display control part 11h for controlling display of the pseudo three-dimensional image of the hollow organ and the reversed image on a monitor 15, a depth value calculating part 11i for setting a virtual line light source in a cavity area of an internal organ and successively calculating the distance from a virtual line light source to a contour point along a running direction of the hollow organ to generate depth value information, a line setting part 11j for setting a line which is perpendicular to a tangent line of a curved line based on the contour area and passes through a contact point on a curved line based on the shape of the contour area, and a recording control part 11k for controlling recording of the reversed image generated by the image generating part 11g into a data storage device (for example, a main memory 12 or a data recording device 13).

The image reading part 11a may receive and read a medical image from the medical image pickup device 2 or the image DB 3 through LAN 4 or from the data recording device 13 equipped to the image display device 10. The image processing program described above is loaded into the main memory 12 and executed by CPU 11, whereby the function thereof is implemented.

The following embodiments will be described by exemplifying a case where a reversed image in which the concavo-convex shape of the inner surface of a large bowel is depicted on the outer surface of the large bowel is generated and displayed on the basis of a medical image obtained by imaging a hollow organ (for example, large bowel) of an examinee. The medical image is not limited to a CT image, but it may be an MRI image or an US image. Furthermore, the hollow organ is not limited to the large bowel, but it may be not only other digestive organs such as an esophagus or a stomach, but also respiratory organs such as bronchial tubes or bronchiole and a blood vessel.

<First Embodiment>

Figure 3:
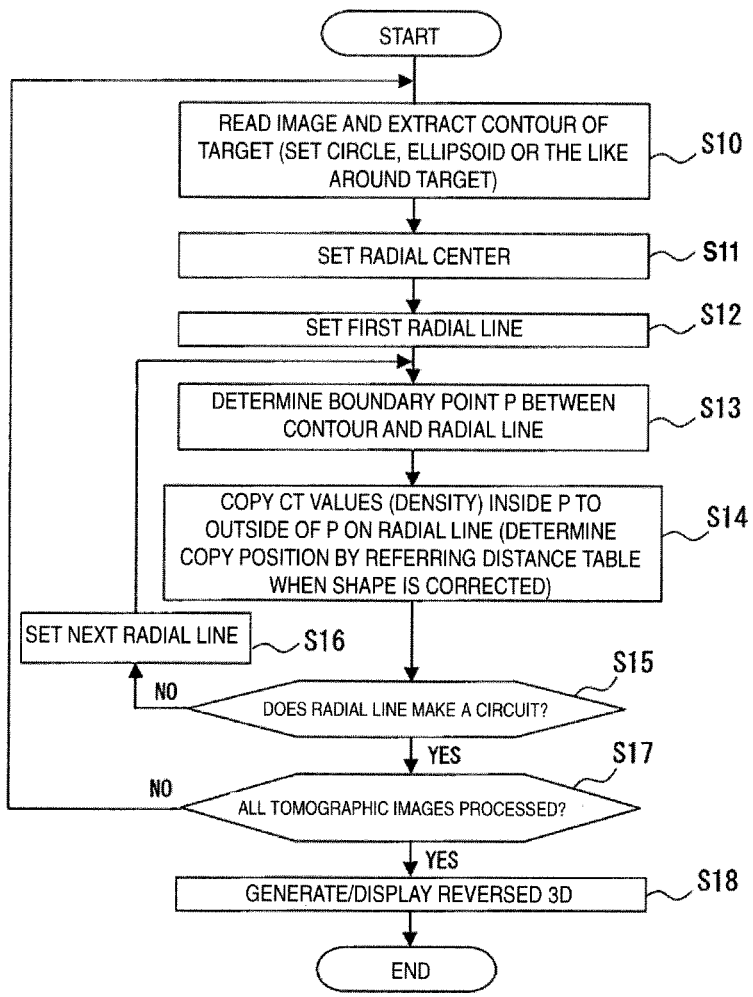
[FIG. 3]
Figure 4A:
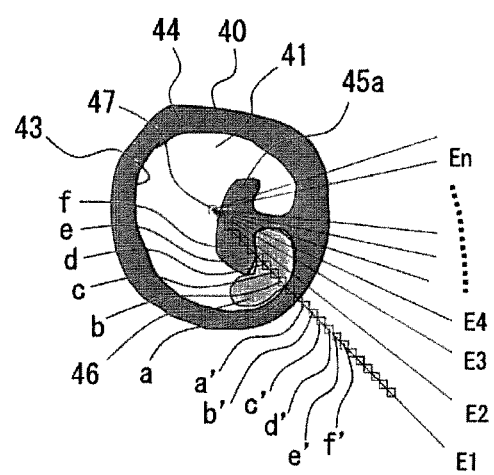
[FIG. 4A]
Figure 4C:
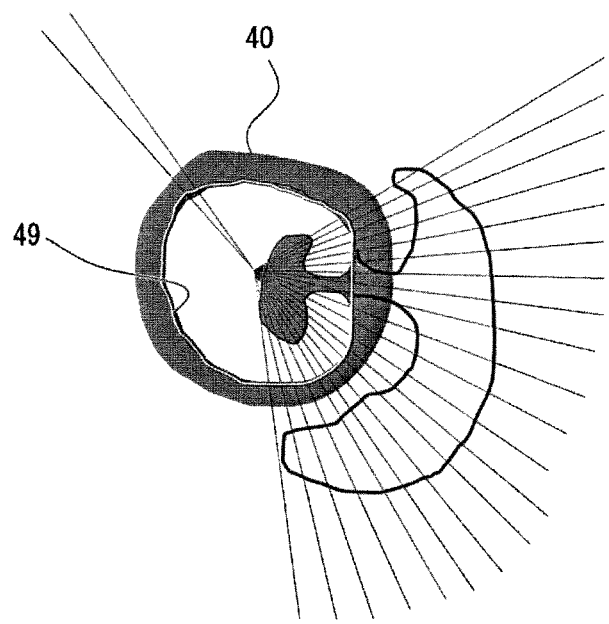
[FIG. 4C]

According to a first embodiment, a radial center is set in a cavity area of a hollow organ whose tomographic image is picked up, and contour points are copied on the basis of the boundary points between radial lines extending from the radial center and a boundary curved line. This embodiment will be described hereunder with reference to FIGS. 3, 4 and 5. FIG. 3 is a flowchart showing the processing flow according to the first embodiment. FIG. 4 is a schematic diagram showing the processing of this embodiment, wherein FIG. 4A shows a state where the radial center and the radial lines are set in the hollow organ extracted from the medical image, FIG. 4B is a schematic diagram showing the processing of copying the contour points, and FIG. 4C is a schematic diagram showing an example of the boundary curved line. FIG. 5 schematically shows a state where the radial center is set at a position deviated from the center of gravity of the cross-section of the hollow organ. FIG. 6 is a schematic diagram showing a reversed image obtained after the processing of FIG. 4B. FIG. 7 is a schematic diagram showing an example in which enlargement/reduction processing is executed when copying is executed.

(Step S10)

The image reading part 11 reads a first tomographic image as a processing target out of a volume image obtained by stacking plural tomographic images. The contour area extracting part 11b executes the extraction processing of a contour area comprising contour points at which the body tissue of the hollow organ is imaged (S10). An area which is displayed substantially annularly with black color in FIG. 4A is a contour area 40 extracted in this step, and it corresponds to an area where the body tissue constituting the hollow organ is imaged.

A cavity area 41 inside the contour area 40 corresponds to an area in which the cavity space of the hollow organ is imaged. An innermost side contour curved line 43 of the contour area 40 represents the shape of the inner surface of the hollow organ, and an outermost side contour curved line 44 represents the shape of the outer surface of the hollow organ. An area in which the innermost side contour curved line 43 is inwardly convex is a polyp area 45a in which polyp occurring inside the hollow organ is imaged. A grey area in the cavity area 41 is a content area 46 in which a content in the hollow organ (large bowel) is imaged.

In FIG. 4A, the radial line setting part 11c uses the outermost side contour curved line 44 as a boundary curved line comprising a point sequence of boundary points P. However, the boundary curved line may be a curved line enveloping the innermost side contour curved line 43, and it may be, for example, a circumscribed circle of the innermost side contour curved line 43, a circle set in the contour area 40, an inscribed circle or circumscribed circle of the outermost side contour curved line 44, a curved line embedded in the contour area, or a circle larger than the outermost side contour curved line 44 as a curved line enveloping the contour area, which will be explained in a fifth embodiment described later. Furthermore, an ellipsoid or a geometrical configuration approximating a circle or ellipsoid may be used in place of the circle.

For example, in FIG. 4B, a circle approximating the outermost side contour curved line 44 is set in the contour area 40.

When the outside of the hollow organ is in contact with another internal organ or visceral fat, there is a case where it is difficult to extract the outermost side contour. In this case, for example, the innermost side contour curved line of the large bowel may be extracted, and a curved line circumscribing the innermost side contour curved line may be set as a boundary curved line.

FIG. 4C shows an example in which a curved line 49 circumscribing the innermost side contour curved line 43 is used as the boundary curved line.

Figure 4D:
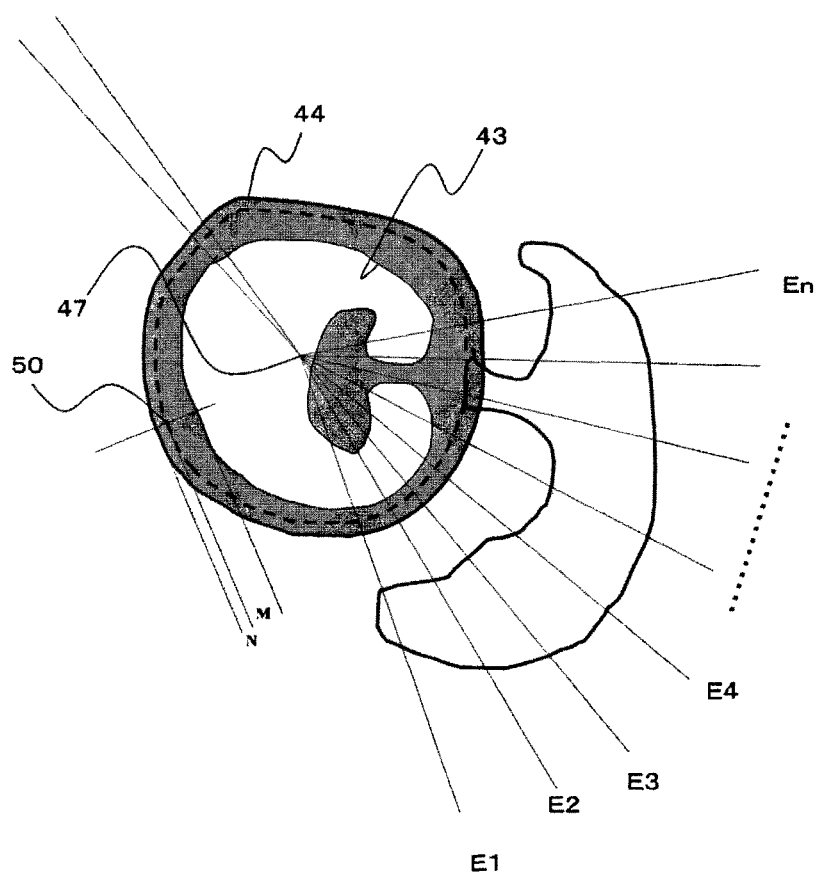
[FIG. 4D]
Figure 5:
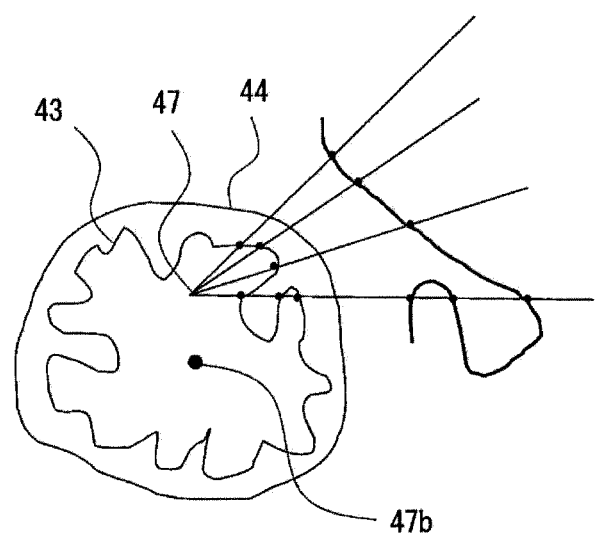
[FIG. 5]

FIG. 4D is a schematic diagram showing an example in which a curved line connecting points of any ratio in the contour area is used as a boundary curved line as an example of a curved line contained in the contour area. A boundary curved line 50 of FIG. 4(d) is a curved line for dividing the thickness of the contour area, that is, the distance from the innermost side contour curved line 43 to the outermost side contour curved line 44 in any ratio. This boundary curved line 50 corresponds to a curved line for dividing the thickness of the body tissue of the hollow organ (for example, the thickness of the large bowel) in ratio of M:N (M, N represent natural numbers). As described above, a curved line contained in a contour area may be used as a boundary curved line.

Each of the boundary curved lines described above is an example, and curved lines having various shapes which are determined on the basis of the shape of the contour area may be used as the boundary curved line.

(Step S11)

The radial line setting part 11c determines the center of gravity of a target internal organ cross-section comprising the contour area 40 and the cavity area 41, and sets a radial center 47 for setting radial lines at the center of gravity (S11).

The radial center is not necessarily required to be the center of gravity, and it maybe located at a position deviated from the center of gravity. FIG. 5 is a schematic diagram showing that binarization processing is executed on a CT image or an MRI image to obtain a binary image containing an innermost side contour curved line and an outermost side contour curved line. However, the radial center 47 may be set to a position deviated from the center of gravity 47b of the target internal organ cross-section as shown in FIG. 5.

(Step S12)

The radial line setting part 11c sets a first radial line, for example, E1 (S12). The radial line is a line extending from the radial center 47 of the step S11 to the contour area 40 (a line extending to the center is also equivalent).

(Step S13)

The copy part 11d determines the outermost side contour point of the contour area 40 on the radial line E1 as a boundary point P (S13).

(Step S14)

The copy part 11d copies image information of each pixel on the radial line E1 at the inside of the boundary point P to a position which is located on the radial line E1 at the outside of the boundary point P so that the distance from the position concerned to the boundary point is equal to the distance from each pixel to the boundary point P (S14).

In FIG. 4A, image information of pixels a, b, c, d, e, f which are arranged at the inside of the boundary point so as to be farther away from the boundary point in this order are copied to pixels a', b', c', d', e', f' which are arranged at the outside of the boundary point so as to be farther away from the boundary line in this order.

FIG. 4B shows the processing that the outermost side contour point of the contour area 40 is set to the boundary point P and each contour point at the inside of the boundary point P is copied to a position which is located at the outside of the boundary point P so as to be far away from the contour point at a distance which is equal to the distance from the boundary point P of a radial line shape to the contour point at the inside.

In FIG. 4, the copy part 11d copies image information onto the memory in which a medical image is developed, however, it may be copied into a memory different from the memory in which the medical image is developed.

FIG. 6 is a diagram showing a reversed image obtained after the processing of FIG. 4B, and also a schematic diagram showing an image after the processing of this step is executed on the basis of a CT image, and CT values at the inside of the outermost side contour curved line 44 are copied to the outside of the outermost side contour curved line 44 as the boundary point. In FIG. 6, an original image at the inside of the outermost side contour curved line 44 is deleted, however, the original image is not necessarily required to be deleted.

CT values are used as the image information when the medical image is a CT image, and density values are used when the medical image is an MRI image or a US image.

Furthermore, in the case of a binary image containing only contour points (line), only the contour points are copied as shown in FIG. 5.

Still furthermore, a blood vessel, etc. are hard to see because they are generally narrow. Therefore, enlargement processing may be executed after copying, that is, after a reversed image is generated, however, enlargement/reduction processing may be executed at the time when copying is executed.

FIG. 7 is a schematic diagram showing an example in which the enlargement/reduction processing is executed at the time when copying is executed, wherein FIG. 7a shows a state where radial lines E1, E2, E3, E4, En are set in an image read in step S10, and FIG. 7b is a schematic diagram showing an example in which enlargement is executed at the time when copying is executed.

The copy part 11d copies image information of a contour point as a copy target to a position which is located at the outside of the boundary point P on the radial line so as to be far away from the boundary point P at a distance which is r-times (corresponding to magnification) as long as the distance from the radial center 47 to the contour point as the copy target.

Accordingly, a reversed 3D image which is r-times of a read-in image in enlargement (reduction) rate can be generated.

(Step S15)

The radial line setting part 11c determines whether the radial line is made to make a circuit. When this determination is YES, it goes to S17, and when this determination is NO, it goes to step S16 (step S15). In this embodiment, 1400 radial lines are set by making the radial line make a circuit of 360°, however, the set number is not limited to this value.

(Step S16)

The radial line setting part 11c sets the next radial line (S16), and then goes to step S13.

(Step S17)

The image reading part 11a determines whether all tomographic images constituting a volume image are read in. When the determination is YES, it goes to step S18, and when the determination is NO, it returns to step S10 to read the next tomographic image (S17).

(Step S18)

The image generating part 11g generates a reversed 3D image comprising a volume rendering 3D image, a surface rendering 3D image, a depth 3D image, etc. by using a tomographic image in which the contour points at the inside of the boundary point P are copied to the outside of the boundary point P. The display control part 11h displays the reversed 3D image on the monitor 15 (S18).

FIG. 8 is a schematic diagram showing a screen display example. FIG. 8a shows a pseudo three-dimensional image 80 which is a conventional pseudo three-dimensional image and which the image generating part 11g constructs by applying shading on the basis of a volume image so that the outer surface thereof is depicted. FIG. 8b shows a reversed 3D image 81 which is constructed by the image generating part 11g through the above processing.

An inwardly convex polyp 82 exists on the inner surface of the hollow organ as an imaging target. However, even when the poly 82 exists in the hollow organ in the pseudo three-dimensional image 80 displayed on the screen of FIG. 8a, it is not displayed on the screen and thus it cannot be seen. In FIG. 8a, the polyp 82 is depicted for explanation, however, it is actually hidden and thus it is not displayed.

However, in the reversed 3D image 81 generated according to this embodiment, as shown in FIG. 8(b), the inner surface of the hollow organ 80 is displayed at the outside, and the polyp 82 is clearly displayed.

Furthermore, in FIGS. 8a, b, soft buttons of a "reversed 3D" button 83 and a "3D" button 84 for switching the display between the pseudo three-dimensional image 80 and the reversed 3D image 81 are provided. When each of the buttons is clicked by the mouse 16, the screen of FIG. 8a can be shifted to the screen of FIG. 8b, or the screen of FIG. 8b can be shifted to the screen of FIG. 8a. In addition to the display switching, parallel display of the screen of FIG. 8a and the screen of FIG. 8b may be adopted.

Furthermore, a rotation button 85 for rotating the display of the pseudo three-dimensional image 80 and the reversed 3D image 81 under display, and a "finish" button 86 for finishing the processing are provided.

Figure 9:
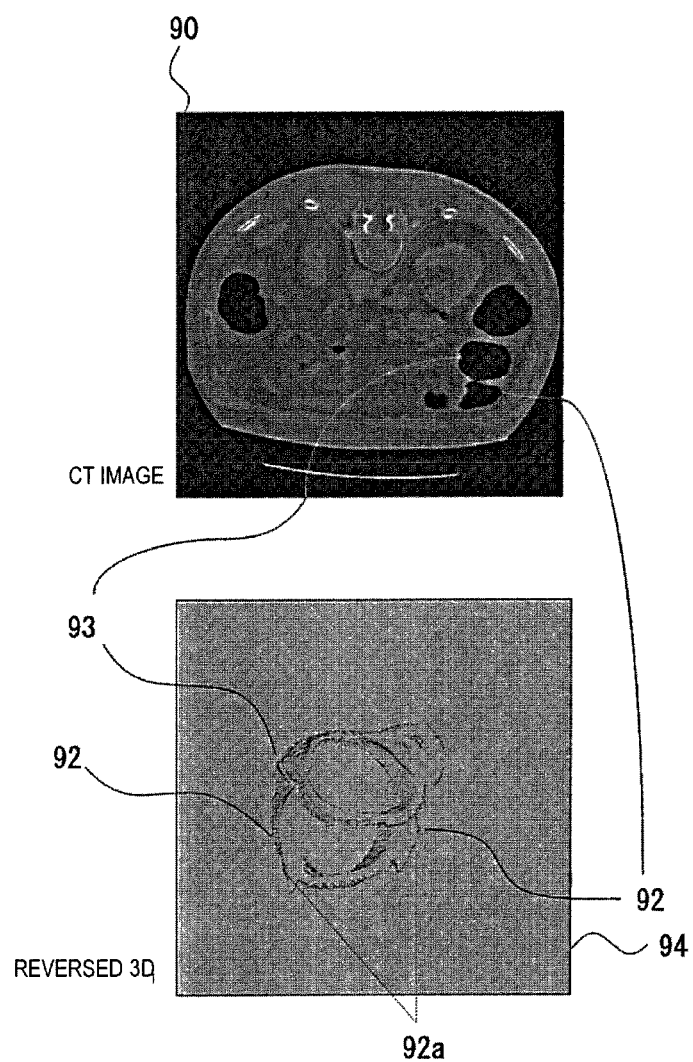
[FIG. 9]

FIG. 9 is a schematic diagram showing a CT image as an original image and a reversed 3D image generated on the basis of a CT image.

The original image 90 is a CT image obtained by imaging an axial cross-section of an examinee, and a corrugation area 92 obtained by imaging corrugation of a large bowel and a polyp 93 occurring on the inner surface of the large bowel exist in each tomographic image. The polyp 93 is imaged to be convex to the cavity area of the large bowel in the tomographic image 90, however, it is depicted to be convex to the outside in the reversed 3D image 94.

The end portion 92a of the corrugation area 92 of the large bowel in the reversed 3D image 94 is displayed as if it is cut out because the copy part 11d restricts the processing so that the copy is stopped halfway without reaching the radial center.

According to this embodiment, the uneven shape on the inner surface of the hollow organ which is hidden and thus is not displayed in the conventional pseudo three-dimensional image can be clearly displayed in the reversed 3D image. Furthermore, the conventional pseudo three-dimensional image and the reversed 3D image are switched to each other in display or parallel-displayed, whereby both the images can be visually compared with each other and thus visibility can be further enhanced.

Second Embodiment

Figure 10:
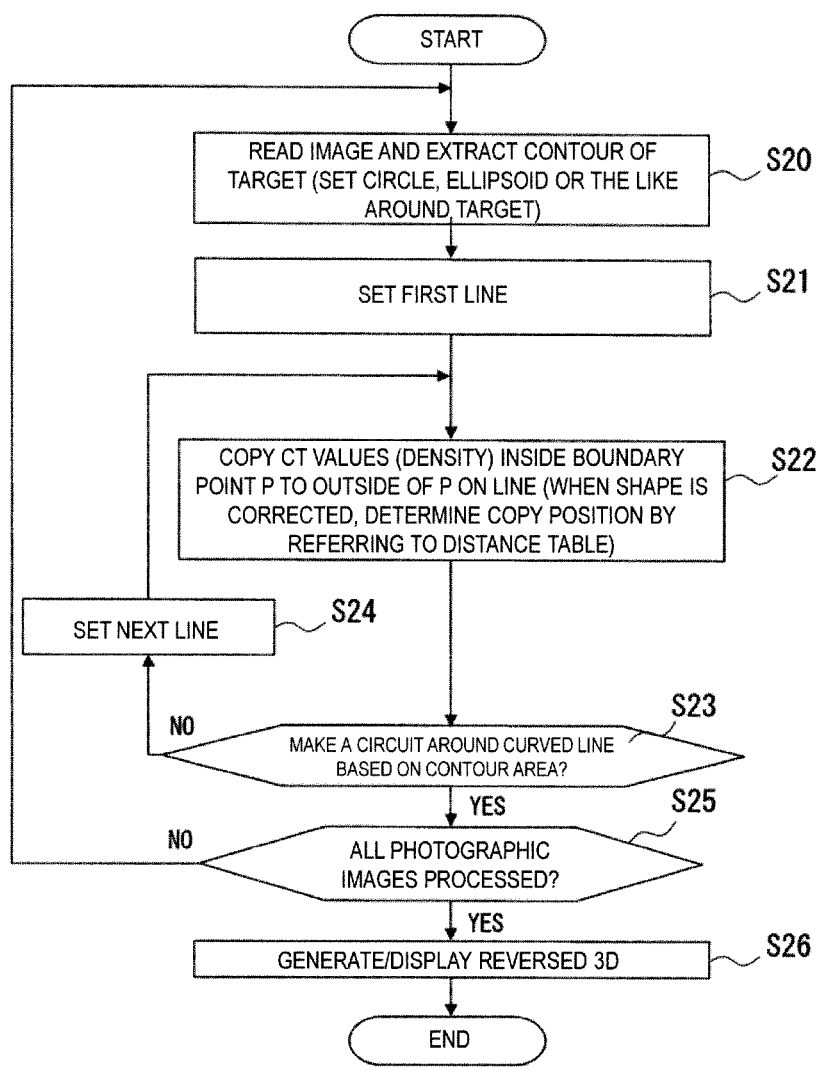
[FIG. 10]

A second embodiment is an embodiment which uses an outermost side contour curved line as a curved line based on the shape of a contour area, and a line vertical to the tangent line of this outermost contour curved line is used. The curved line based on the shape of the contour area is not limited to the outermost contour curved line. This embodiment will be described on the basis of FIGS. 10 and 11. FIG. 10 is a flowchart showing the flow of the processing of the second embodiment. FIG. 11 is a schematic diagram showing the processing of the second embodiment, wherein FIG. 11a is a schematic diagram showing an original image comprising a CT image, and FIG. 11b shows an example in which FIG. 11a is subjected to binarization processing, the outermost side contour point of the binary image is set as a boundary point P and the binary image is copied to the outside of the boundary point P.

(Step S20)

In step S20, the image reading part 11 reads an image and the contour area extracting part 11b executes the processing of extracting a contour area comprising contour points at which the body tissue of the hollow organ is imaged (S20).

(Step S21)

The line setting part 11j sets a first line which is orthogonal to the tangent line of an outermost side contour curved line 110 and passes through a contact point, for example, T1 (S21).

(Step S22)

The copy part 11d copies image information of each pixel on the line T1 at the inside of the outermost side contour point (corresponding to the boundary point) P to a pixel at a position which is located on the line T1 at the outside of the outermost side contour point P and spaced from the outermost side contour point P at the distance which is equal to the distance from each pixel to the boundary point P (S22).

(Step S23)

In step S23, it is determined whether lines are set for all the points on the outermost counter curved line. When the determination is YES, the processing goes to step S25, and when the determination is NO, the processing goes to step S24.

(Step S24)

In step S24, with respect to an adjacent pixel point on the outermost contour curved line, the line setting part 11j sets a line orthogonal to the tangent line at the pixel point concerned.

(Step S25)

Lines are set for all the points on the outermost contour curved line, and copying is executed, whereby the data necessary to generate a two-dimensional reversed image are recorded into the main memory 12 or the data recording device 13 by the recording control part 11k.

Then, it is determined whether the processing on all the tomographic images is completed. When the determination is YES, the processing goes to step S26, and when the determination is NO, the processing returns to step S20.

(Step S26)

The image generating part 11g collects data necessary to generate a two-dimensional reversed image recorded/saved by the storage control part 11k by only the amount corresponding to the number of tomographic images, and generates a pseudo three-dimensional reversed image. Then, the display control part 11h displays the pseudo three-dimensional reversed image on the monitor 15.

The image generating part 11g may generate/display a two-dimensional reversed image in place of the pseudo three-dimensional reversed image. Furthermore, the two-dimensional reversed image may be generated/displayed every tomographic image. Furthermore, plural two-dimensional images may be selectively or simultaneously displayed or cine-displayed.

Still furthermore, both the pseudo three-dimensional reversed image and the two-dimensional reversed image may be generated/displayed.

According to this embodiment, the reversed image can be generated without setting the radial center.

In the step S25, the embodiment in which the recording control part 11k records the data necessary to generate the two-dimensional reversed image into the main memory 12 or the data recording device 13 and the image generating part 11g generates only the pseudo three-dimensional reversed image without generating any pseudo two-dimensional reversed image, or conversely it generates only the two-dimensional reversed image or generates both of the pseudo three-dimensional and two-dimensional reversed images is not limited to the second embodiment, but may be applied to the other embodiments.

<Third Embodiment>

A third embodiment is an embodiment of executing copying so that an inside contour point (copy source contour point) and an outside point (copy destination contour point) are located asymmetrically with respect to a boundary point as a reference point. The content of the processing of this embodiment will be described hereunder with reference to FIG. 12. The processing of this embodiment corresponds to the processing described in parentheses of the step S14 of FIG. 3 and the step S22 of FIG. 10.

FIG. 12 is a schematic diagram showing the content of the processing of the third embodiment. When a polyp 120a of FIG. 12 is copied to a symmetrical position with respect to a boundary curved line 121, the polyp 120a of FIG. 12a is deformed in shape like a polyp 120b of FIG. 12b due to an opening degree of radial lines. Therefore, in this embodiment, the copying is executed so that the inside contour point and the copy destination point are located at asymmetrical positions with respect to a boundary point (outermost side contour point).

Specifically, a value at an inside position spaced from the boundary point P at a distance D is copied to an outside position of D·m(D). The magnification m(D) is selected or input by a mouse on a screen of FIG. 12d. Each of curved lines c1, c2, c3 and c4 of the screen of FIG. 12d is a magnification curved line representing the magnification m(D) corresponding to the distance D from the boundary point P, and it is a curved line for determining the magnification so that the distance to the position of the copy destination increases as the position approaches to the center of gravity of the cross-section of the target internal organ or the radial center.

By clicking any one of these magnification curved lines with the mouse, the copy part 11d measures the distance D from the boundary point P to the inside contour point, determines the magnification m(D) corresponding to the distance D with respect to the selected magnification curved line, and copies the image information of the inside contour point to the coordinate of the distance D·m(D) from the boundary point P with respect to the radial lines. Accordingly, a reversed image in which the deformation caused by the opening angle of the radial lines is less can be generated.

<Fourth Embodiment>

A fourth embodiment is an embodiment of setting another window (hereinafter referred to as "reverse window") on a pseudo three-dimensional image, and displaying in the reverse window a reversed 3D image in which the site corresponding to the reverse window of the pseudo three-dimensional image is reversed.

FIG. 13 is a schematic diagram showing a screen display example displayed in the fourth embodiment.

As shown in FIG. 13a, an initial screen is a screen on which a conventional pseudo three-dimensional image whose outer surface is depicted is displayed.

When a user drags on the pseudo three-dimensional image displayed on the screen by the mouse 16 to specify an area, the display frame setting part 11f sets/displays a display frame of the reverse window 130 in the specified area.

Subsequently, the image generating part 11g generates a reversed image in which the site of the pseudo three-dimensional image of the area specified by the user is reversed. The display control part 11h displays the generated reversed 3D image in the reverse window 130.

According to this embodiment, only a desired site can be subjected to reversed 3D display. For example, in a case where existence of a polyp on the inner surface of the internal organ is suspected when a pseudo three-dimensional image which is subjected to volume-rendering is visually recognized, the convenience of the diagnosis can be enhanced by reversing only the site concerned and checking the concavoconvex shape of the inner surface.

<Fifth Embodiment>

A fifth embodiment is an embodiment in which a set circle larger than an outermost side contour curved line is set as a boundary curved line.

Specifically, in the step S10 of the first embodiment, the radial line setting part 11c sets as a boundary curved line a set circle which is further larger than the innermost side contour curved line of the target internal organ. Then, in step S13, the radial line setting part 11c determines the cross point between the set circle and the radial line as the boundary point P.

Furthermore, in the second embodiment, in step 21, the radial line setting part 11c determines the tangent line of the set circle, and sets a radial line which is orthogonal to the tangent line and passes through the contact point on the set circle. In each of subsequent steps, this contact point is used as the boundary point P.

Figure 14:
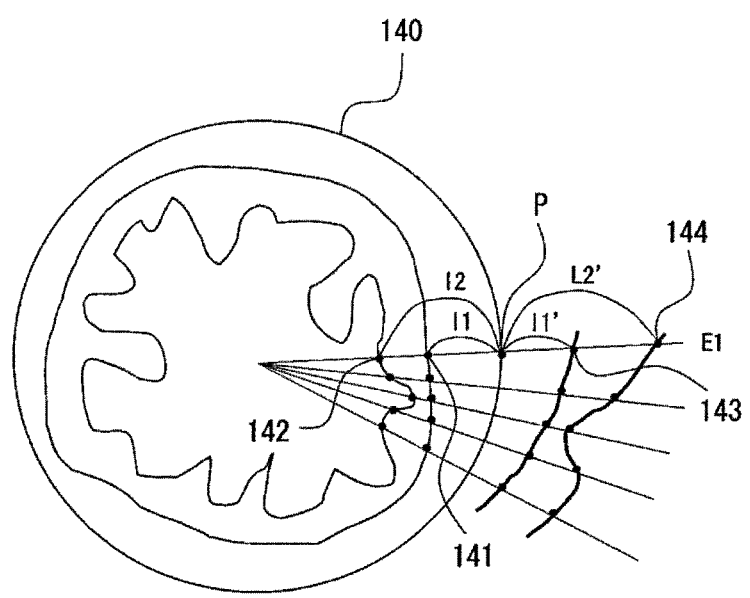
[FIG. 14]

FIG. 14 is a schematic diagram showing an example in which a circle 140 which is further larger than the outermost side contour curved line 141 is used as a boundary curved line. The copy part 11d copies the image information of the outermost side contour point 141 on the radial line E1 to an outside position 11' on the radial line E1 which is far away from the boundary point P at the distance equal to the distance 11 from the outermost side contour point 141 to the boundary point P, thereby obtaining a copy destination point 143.

Likewise, the copy part 11d copies the image information of the innermost side contour point 142 to an outside position 12' on the radial line E1 which is far away from the boundary point P at the distance equal to the distance 12 from the innermost side contour point 142 to the boundary point P, thereby obtaining a copy destination point 144.

According to this embodiment, by copying the innermost side contour curved line and the outermost side contour curved line, a reverse image in which the outer surface and inner surface of the hollow organ are reversed can be generated at a position which is far away from the target internal organ area of the original image.

<Sixth Embodiment>

A sixth embodiment is an embodiment in which a user inputs a radial center point sequence by a mouse.

In a case where a pseudo three-dimensional image generated on the basis of a volume image is displayed on the monitor 15, when a user traces the inside of a hollow organ by the mouse 16, the radial line setting part 11c sets a traced coordinate to the radial center point sequence. Furthermore, the radial line setting part 11c may determine a point-of-view sequence of a virtual endoscope used when a virtual endoscope image is generated on the basis of a volume image, and set this point-of-view sequence as a radial center point sequence.

Figure 15:
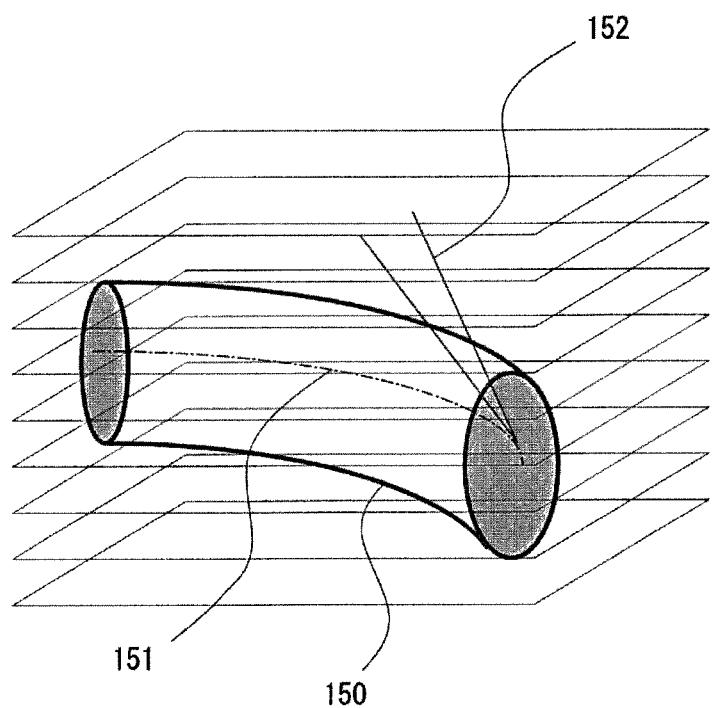
[FIG. 15]

FIG. 15 is a schematic diagram showing a processing example of this embodiment. In the volume image of FIG. 15, a hollow organ 150 which runs substantially in parallel to cross-sectional planes is imaged. When a user traces along a one-dotted chain line by the mouse 16, the radial line setting part 11c sets a radial center point sequence 151.

The radial line setting part 11c sets a radial line 152 starting from each point of the radial center point sequence 151 as a starting point.

The copy part 11d executes copy processing by using the radial line 152. In general, in the case of the processing of copying image information at an inside position with respect to the boundary point P to an outside position, with respect to a hollow organ running substantially in parallel to a cross-sectional plane, it is copied to a plane (memory) in a direction vertical to the hollow organ as a copy destination as shown in FIG. 15. When viewed from the original tomographic image, this copying is executed over plural tomographic images, and thus the copying is three-dimensionally executed.

According to this embodiment, the user can input a radial center point sequence on a pseudo three-dimensional image. Furthermore, even when a virtual endoscope image is generated, the point-of-view sequence thereof can be diverted as the radial center point.

<Seventh Embodiment>

A seventh embodiment is an embodiment in which a reversed image is generated by using a method of generating a depth image. The seventh embodiment will be described hereunder with reference to FIG. 16. The description will be made hereunder along an example of FIG. 16.

The image reading part 11a reads a medical image comprising a volume image obtained by stacking, in a body axis direction, plural tomographic images CT1, CT2, CT3, . . . which are obtained by imaging a hollow organ 160 of an examinee.

The contour area extracting part 11b extracts contour points at the inside as an area in which the inner surface 161 of the hollow organ 160 is imaged.

The depth value calculating part 11i sets a virtual line light source at the first position 162a in a cavity area in which a cavity space of the hollow organ is imaged, and sets a projection line a so that the projection line a extends from the position 162a to the inner surface 161. Then, the distance from the position 162a to the inside contour point is calculated along the projection line a. The calculation of the distance is executed over 360° like projection lines b, c, d, e, f, g, . . . , z. Then, depth value information for associating a position 162a (depth value) in the running direction of the hollow organ of the virtual line light source with the distance to the contour point which is calculated at the position concerned is generated, and stored in the main memory 12.

Subsequently, the depth value calculating part 11*i* calculates the distance from the virtual line light source to the inside contour point again at a new position 162*b* which goes from the first position 162*a* of the virtual line light source along the running direction of the hollow organ, and stores the calculated distance. This processing is executed overall the areas 162*c*, ..., 162*d*, 162*e* of the hollow organ whose reversed image is desired to be displayed.

With respect to this depth value information, the distance to the contour point is relatively smaller when the inner surface of the hollow organ has a convex-shape, and is relatively larger when the inner surface of the hollow organ has a concave-shape. Therefore, the depth value information contains information on the concavo-convex shape of the inner surface.

On the basis of this depth information, 165 of FIG. 16 represents an image which is shaded on the basis of the distance from the virtual line light source to the inner surface with respect to a two-dimensional planar image 165 which is coordinate-transformed so that the distance in the running direction of the hollow organ 160 represents the y-axis direction and the peripheral direction of the hollow organ 160 represents the x-axis direction. In this image, the concavo-convex shape of the inner surface cannot be represented.

Therefore, according to this embodiment, as indicated by 168 of FIG. 16, the image generating part 11*g* coordinate-transforms the depth value (the distance in the running direction of the hollow organ) to the height of the reversed 3D image and also coordinate-transforms the length in the peripheral direction of the hollow organ 160 to the length in the peripheral direction of the reversed 3D image. Furthermore, the outer surface of the image after the coordinate transformation is shaded in accordance with the distance from the virtual line light source to the inside contour point which is calculated every position in the running direction of the hollow organ, thereby generating a reversed image in which the shading of the inner surface of the hollow organ is depicted on the outer surface.

The display control part 111 displays the reversed 3D image 168 on the monitor 15.

According to this embodiment, the reversed 3D image in which the unevenness on the inner surface of the hollow organ is depicted as unevenness of the outer surface by using shading can be generated, and the visibility of the inner surface can be enhanced. Furthermore, the reversed 3D image can be generated by diverting depth value information used to generate a conventional depth image.

In each of the above embodiments, the boundary point P is set as a center, and image information at the inside the boundary point P is copied to the outside of the boundary point P to generate a reversed 3D. However, conversely, the innermost side contour point may be used as the boundary point P, the innermost side contour point (boundary point P) may be set as a center, and image information at the outside of the boundary point P may be copied to the inside of the innermost side contour point (boundary point P) to generate a reversed 3D.

For example, in the second embodiment, a line vertical to the tangent line of the innermost side contour curved line is used in place of use of the line vertical to the tangent line of the outermost side contour curved line, the innermost side contour point is set as the boundary point P, and image information at the outside of the boundary point P is copied to the inside of the boundary point P.

In the first embodiment, the innermost side contour point is used as the boundary point, the innermost side contour point is set as the boundary point P, and image information at the outside of the boundary point P is copied to the inside of the boundary point P.

When the first embodiment and the second embodiment described above are applied, any one of an inscribed circle of the innermost side contour curved line, a circle located at the inside of the innermost contour curved line, an ellipsoid and a geometric curved line approximating an ellipsoid may be set as a boundary curved line in place of the innermost side contour curved line, and a line which is orthogonal to the tangent line of the boundary curved line concerned and passes through the contact point on the boundary curved line may be set.

Accordingly, a reversed 3D in which the innermost side contour curved line serves as an outer edge can be generated. In this reversed 3D, for example, a polyp which is generated in a convex-shape on the inner surface of a large bowel is depicted in a concave-shape, and a concave-shape of the inner surface (for example, a depression type tumor) is depicted in a convex-shape in the reversed 3D.

As described above, the reversed 3D of each of the above embodiments is the reversed 3D in which concavity and convexity are reversed, however, the same action and effect as the reversed 3D of each of the above embodiments can be attained in the point that the concavo-convex shape of the inner surface of the large bowel can be depicted on the outer surface.

DESCRIPTION OF REFERENCE NUMERALS 1 image display system, 2 medical image pickup device, image data base (image DB), 4 LAN, 10 image processing device, 11 CPU, 12 main memory, 13 data storage device, 14 display memory, 15 monitor, 16 mouse, 16*a* controller, 17 keyboard, 18 network adaptor, 19 bus

The invention claimed is:

1. An image display device, characterized by comprising:
   contour area extracting means that extracts a contour area comprising plural contour points at which a body tissue of an examinee is imaged, from a medical image obtained by imaging a hollow organ having a cavity space inside the body tissue of the examinee;
   radial line setting means that sets a radial center in a cavity area of the medical image in which the cavity space is imaged, sets a radial line extending from the radial center to the contour area and sets a boundary point at one point on the radial line;
   copy means that copies image information of a pixel that is on the radial line and inside of the boundary point to a pixel that is on the radial line and outside of the boundary point;
   image generating means that generates, on the basis of the copied image information of the pixel point, a reversed image in which an area at the inside of the boundary point is depicted at the outside of the boundary point; and
   image display means that displays the reversed image.

2. An image display device, characterized by comprising:
   contour area extracting means that extracts a contour area comprising plural contour points at which a body tissue of an examinee is imaged, from a medical image obtained by imaging a hollow organ having a cavity space inside the body tissue of the examinee;
   line setting means that sets a line being perpendicular to a tangent line of a curved line based on a shape of the contour area and passing through a contact point on a curved line based on a shape of the contour area;

copy means that copies image information of a pixel that is on the radial line and inside of the contact point to a pixel that is on the line and outside of the contact point;

image generating means that generates, on the basis of the copied image information of the pixel point, a reversed image in which an area at the inside of the contact point is depicted at the outside of the contact point; and image display means that displays the reversed image.

3. The image display device according to claim 2, wherein:
the line setting means sets a line being perpendicular to a tangent line of a curved line based on a shape of the contour area and passing through a contact point on a curved line based on a shape of the contour area; and the copy means copies image information at a pixel point located on the line and at the inside of the contact point onto the line at the outside of the contact point.

4. The image display device according to claim 2, wherein the line setting means sets a line which is perpendicular to a tangent line of an innermost side contour curved line comprising an innermost side contour point sequence of the contour area and passes through an innermost side contour point serving as a contact point on the innermost side contour curved line; and the copy means copies image information at a pixel point located on the line and at the outside of the innermost side contour point onto the line at the inside of the innermost side contour point.

5. The image display device according to claim 1, wherein the copy means copies a pixel point at the inside so that the boundary point or the contact point, a contour point at the inside of an outermost side contour point and a copy pixel point to which a pixel point at the inside is copied are in asymmetrical positional relationship on the radial line with respect to the boundary point or the outermost side contour point, or the copy means copies a pixel point at the outside so that a pixel point at the outside of the innermost side contour point and a copy pixel point to which a pixel point at the outside is copied are in asymmetrical positional relation on the line with respect to the innermost side contour point.

6. The image display device according to claim 1, wherein the radial line setting means sets, as a boundary curved line, any one curved line or circle of an outermost side contour curved line comprising a point sequence of outermost side contour points, a circumscribed circle or inscribed circle of the outermost side contour curved line, an innermost side contour curved line comprising a point sequence of innermost side contour points of the contour area, a circumscribed circle of the innermost side contour curved line, a curved line enveloped in the contour area, a circle embracing the contour area and a curved line based on the shape of the contour area, or an ellipsoid and a geometric curved line approximating the ellipsoid in place of the circle as the boundary point, and a crosspoint between the radial line and the boundary curved line is set as a boundary point.

7. The image display device according to claim 1, wherein the medical image is a volume image obtained by stacking a plurality of tomographic images in a body axial direction of the examinee, the contour area extracting means, the radial line setting means and the copy means execute the corresponding processing on at least one of the plurality of tomographic images, and the image generating means generates a three-dimensional reversed image on the basis of copied image information of pixel points in the tomographic images.

8. The image display device according to claim 7, wherein the image generating means generates on the basis of the volume image a pseudo three-dimensional image in which an outer surface of the hollow organ is depicted, the image display means has display frame setting means that displays a pseudo three-dimensional image of the hollow organ, and sets a display frame for displaying a reversed image corresponding to a site of the pseudo three-dimensional image, the image generating means generates the three-dimensional reversed image corresponding to the side of the pseudo three-dimensional image in the display frame, and the image display means displays the three-dimensional reversed image in the display frame.

9. The image display device according to claim 7, wherein the image generating means generates on the basis of the volume image a pseudo three-dimensional image in which an outer surface of the hollow organ is displayed, and the image display means subjects a pseudo three-dimensional image of the hollow organ and the three-dimensional reversed image to parallel display or switching display.

10. The image display device according to claim 8, further comprising means that inputs a radial center line comprising a point sequence of the radial center onto the pseudo three-dimensional image displayed by the image display means.

11. The image display device according to claim 1, further comprising internal organ specifying means that specifies a desired imaged internal organ in the medical image, wherein the contour area extracting means extracts a contour area of the specified internal organ.

12. The image display device according to claim 1, wherein:

the contour area extracting means extracts an innermost side contour point out of the contour area, and the medical image comprises a volume image obtained by stacking, in a body axis direction of the examinee, a plurality of tomographic images which are obtained by imaging a hollow organ having a cavity space inside the body tissue of the examinee;

wherein the image display device further comprises depth calculating means that sets, in the medical image, a virtual line light source in a cavity area in which the cavity space is imaged, calculates the distance from the virtual line light source to the innermost side contour point at each position of the virtual line light source while moving the position of the virtual line light source along a running direction of the hollow organ, and calculates depth value information for associating the position of the virtual line light source in the running direction of the hollow organ with the distance from the position concerned to the innermost side contour point; and the image generating means coordinate-transforms the depth value to the distance in the running direction of the hollow organ on the basis of the depth value information, and shades the outer surface of a coordinate-transformed image in accordance with the distance at each position in the running direction of the hollow organ, thereby generating a reversed image in which the shading of an inner surface of the hollow organ is depicted on an outer surface of the hollow organ.

13. An image display method, characterized by comprising:

a step of extracting a contour area comprising a plurality of contour points at which a body tissue of an examinee is imaged, from a medical image obtained by imaging a hollow organ having a cavity space inside the body tissue of the examinee;

a step of setting a radial center in a cavity area of the medical image in which the cavity space is imaged, setting a radial line extending from the radial center to the contour area and setting a boundary point at one point on the radial line;

a step of copying image information of a pixel that is on the radial line and inside of the boundary point to a pixel that is on the radial line and outside of the boundary point;

a step of generating, on the basis of the copied image information of the pixel point, a reversed image in which an area at the inside of the boundary point is depicted at the outside of the boundary point; and a step of displaying the reversed image.

14. An image display program stored in a non-transitory computer readable medium and including instructions executable by a computer and making the computer execute the image display method according to claim 13.

* * * * *